(12) United States Patent
Hartley et al.

(10) Patent No.: US 7,292,891 B2
(45) Date of Patent: Nov. 6, 2007

(54) BIONET FOR BILATERAL COCHLEAR IMPLANT SYSTEMS

(75) Inventors: Lee F Hartley, Castaic, CA (US); Michael A Faltys, Northridge, CA (US)

(73) Assignee: Advanced Bionics Corporation, Valencia, CA (US)

( * ) Notice: Subject to any disclaimer, the term of this patent is extended or adjusted under 35 U.S.C. 154(b) by 990 days.

(21) Appl. No.: 10/218,615

(22) Filed: Aug. 13, 2002

(65) Prior Publication Data

US 2003/0036782 A1 Feb. 20, 2003

Related U.S. Application Data

(60) Provisional application No. 60/313,694, filed on Aug. 20, 2001.

(51) Int. Cl.
*A61N 1/36* (2006.01)
(52) U.S. Cl. ...................................................... 607/57
(58) Field of Classification Search ............ 607/55–57, 607/136, 137; 600/379
See application file for complete search history.

(56) References Cited

U.S. PATENT DOCUMENTS

| | | | |
|---|---|---|---|
| 4,232,679 A | 11/1980 | Schulman | |
| 4,400,590 A | 8/1983 | Michelson | |
| 4,515,158 A | 5/1985 | Patrick et al. | |
| 4,532,930 A * | 8/1985 | Crosby et al. | 607/57 |
| 4,570,130 A | 2/1986 | Grindel et al. | |
| 4,577,641 A | 3/1986 | Hochmair et al. | |
| 4,592,359 A | 6/1986 | Galbraith | |
| 4,612,934 A | 9/1986 | Borkan | |
| 4,617,913 A | 10/1986 | Eddington | |
| 4,745,309 A | 5/1988 | Waller, Jr. | |
| 4,755,774 A | 7/1988 | Heck | |
| 4,901,353 A | 2/1990 | Widin | |
| 4,947,844 A | 8/1990 | McDermott | |
| 5,095,904 A | 3/1992 | Seligman et al. | |
| 5,317,284 A | 5/1994 | Yang | |
| 5,479,522 A | 12/1995 | Lindemann et al. | |
| 5,522,865 A | 6/1996 | Schulman et al. | |
| 5,601,617 A * | 2/1997 | Loeb et al. | 607/56 |

(Continued)

FOREIGN PATENT DOCUMENTS

EP    0241101 A1    9/1984

(Continued)

*Primary Examiner*—George R. Evanisko
(74) *Attorney, Agent, or Firm*—Bryant R. Gold; Victoria A. Poissant

(57) ABSTRACT

A system for allowing bilateral cochlear implant systems to be networked together. An adapter module that forms part of the system allows two standalone BTE units to be synchronized both temporally and tonotopically in order to maximize a patients listening experience. The system further allows a peer-to-peer network and protocol that includes two BTE units during normal operation, or two BTE units plus a host controller (PC, PDA, etc. . . . ) during fitting. The bilateral cochlear network includes four main components: (a) a communications interposer adapted to be inserted between the BTE battery and the BTE housing or modified BTE devices; (b) a communication channel over which communication takes place between the connected devices, including the protocol governing access to such channel; (c) the synchronization mechanisms used to achieve synchronization between the connected devices; and (d) a bilateral fitting paradigm.

7 Claims, 16 Drawing Sheets

U.S. PATENT DOCUMENTS

| | | |
|---|---|---|
| 5,603,726 A | 2/1997 | Schulman et al. |
| 5,626,629 A | 5/1997 | Faltys et al. |
| 5,721,783 A | 2/1998 | Anderson |
| 5,758,651 A | 6/1998 | Nygard et al. |
| 5,805,871 A | 9/1998 | Baxter |
| 5,824,022 A * | 10/1998 | Zilberman et al. ............ 607/57 |
| 5,876,425 A | 3/1999 | Gord et al. |
| 5,991,419 A | 11/1999 | Brander |
| 6,002,966 A | 12/1999 | Loeb et al. |
| 6,067,474 A | 5/2000 | Schulman et al. |
| 6,068,652 A | 5/2000 | Cohen et al. |
| 6,157,861 A | 12/2000 | Faltys et al. |
| 6,181,969 B1 | 1/2001 | Gord |
| 6,195,585 B1 | 2/2001 | Karunasiri et al. |
| 6,219,580 B1 | 4/2001 | Faltys et al. |
| 6,272,382 B1 | 8/2001 | Faltys et al. |
| 6,289,247 B1 | 9/2001 | Faltys et al. |
| 6,308,101 B1 | 10/2001 | Faltys et al. |
| 6,449,372 B1 | 9/2002 | Greminger |
| 6,505,076 B1 | 1/2003 | Tziviskos et al. |
| 6,549,633 B1 | 4/2003 | Westermann |
| 6,697,674 B2 * | 2/2004 | Leysieffer .................... 607/57 |
| 6,735,474 B1 | 5/2004 | Loeb et al. |
| 6,775,389 B2 | 8/2004 | Harrison et al. |
| 6,826,430 B2 | 11/2004 | Faltys et al. |
| 6,842,647 B1 | 1/2005 | Faltys et al. |

FOREIGN PATENT DOCUMENTS

| | | |
|---|---|---|
| EP | 0241101 B1 | 9/1984 |
| WO | WO9501709 | 12/1995 |
| WO | WO9701314 A1 | 1/1997 |
| WO | WO9709863 A1 | 3/1997 |

* cited by examiner

BIONET FOR BILATERAL COCHLEAR IMPLANT SYSTEMS

The present application claims the benefit of U.S. Provisional Patent Application Ser. No. 60/313,694, filed Aug. 20, 2001, which application, including its Appendix A, is incorporated herein by reference in its entirety.

BACKGROUND OF THE INVENTION

The present invention relates to bionic ear implants, and more particularly to an ear level high resolution bilateral programming system for use with a bionic ear implant.

A new generation of cochlear implants, commonly referred to as a "bionic ear" implant, has recently been introduced to the cochlear implant community. A representative bionic ear implant is the CII Bionic Ear™ cochlear implant system introduced by Advanced Bionics Corporation, of Sylmar Calif. A bionic ear implant is capable of delivering electrical stimulation to a patient at rates and resolutions which surpass that of conventional cochlear implants.

Early research indicates that cochlear implant patients will benefit from additional synchronized and processed speech information conveyed to the brain via both the right and left auditory nerve pathways. Several configurations are available to implement such a system, including, e.g.: (a) bilateral implants controlled by a single master speech processor; (b) bilateral implants driven by independent external speech processors; and (c) bilateral implants driven by synchronized external speech processors. The present invention relates primarily to configurations (b) & (c).

Of significance to configuration (c) is its ability to interface with patients who use presently available technology platforms; specifically ear level early-generation speech processors. (The early-generation speech processors are referred to herein as "CI" processors, whereas the more recent bionic ear processors are referred to as the "CII" processors.) With or without a hardware change to a standalone behind-the-ear (BTE) processor, there is a need for an adapter module whereby two standalone BTE units may be synchronized both temporally and tonotopically to maximize the CI patients listening experience. There is also a need for a peer-to-peer network and protocol consisting of two BTE units during normal operation, or two BTE units plus a host controller (PC, PDA, etc. . . . ) during a fitting session.

SUMMARY OF THE INVENTION

The present invention addresses the above and other needs by providing an adapter module that allows two standalone BTE units to be synchronized both temporally and tonotopically in order to maximize the CI patients listening experience. Further, the present invention provides a peer-to-peer network and protocol that consists of two BTE units during normal operation, or two BTE units plus a host controller (PC, PDA, etc. . . . ) during fitting.

The system provided by the invention includes (a) a communications interposer adapted to be inserted between the BTE battery and the BTE housing or modified BTE devices; (b) a communication channel over which communication takes place between the connected devices, including the protocol governing access to such channel; (c) the synchronization mechanisms used to achieve synchronization between the connected devices; and (d) a bilateral fitting paradigm. Each of these four components of the invention are summarized below.

(a) Communications Interposer. The communications interposer is a plug-in module designed for use with the Clarion® BTE (a CI device). It interfaces mechanically to the existing clinicians programming interface (CPI) contacts found on the underside of a standard platinum series BTE. The interposer module contains the interface electronics to the physical layer (any necessary antennae or connectors) and a replicated battery port on its underside to allow insertion as usual of a BTE battery.

(b) Communication Channel. The communication channel may be a wired or wireless link configured to use proprietary technology (e.g. the implantable speech processor's 10.7 MHz ITEL channel) or industry standard channels (e.g. the newly allocated 400 MHz medical band, Bluetooth, 802.11, etc. . . . ). One preferred embodiment uses wired interconnections of multiple speech processors and a fitting station via the buffered serial ports that are standard on Texas Instruments DSP products. In the case of wired links, interference is not a problem and the fundamentals of an enhanced packet protocol are utilized. For a wireless embodiment, bandwidth and interference issues bound the ultimate capability and robustness of the system. Any time there is a need to maintain communications in real time between two operating processors, there are many tradeoffs to consider, leaving certain implementations fundamentally superior to others. Conversely, developing new applications to run over an industry standard link utilizing industry standard protocols (e.g. Bluetooth) may simplify the development of new applications.

(c) Synchronization. The raw bandwidth and necessary protocol overhead of a chosen physical medium dictates the nature of information that can be passed over the network in real time. This, in turn, limits the degree to which parallel speech processors can synchronize their activities and/or share information. In a preferred embodiment, a maximally efficient data link layer is used that allows for arbitrary data exchange and device synchronization. Disadvantageously, varying degrees of reduced functionality are mandated as the system's communication bandwidth is reduced and/or as protocol overheads increase. To minimize such reduced functionality, several steps are taken. First, a fitting mechanism is used that tonotopically ranks electrode contact position in the contra-lateral cochlea, followed by assignment of audio frequency bands to those optimal contacts. Second, an operational mode is used that offers noise cancellation and directional hearing by making use of phase information available from the contra-lateral microphones. Third, an operational mode is described for listening in stereo.

(d) Bilateral fitting Paradigm. A fitting procedure, based on trans-cochlear pitch discrimination, is used so as to reduce channel interaction and optimally interleave channel information across available electrode contacts.

BRIEF DESCRIPTION OF THE DRAWINGS

The features and advantages of the present invention will be more apparent from the following more particular description thereof, presented in conjunction with the following drawings, wherein.

Figure 1:
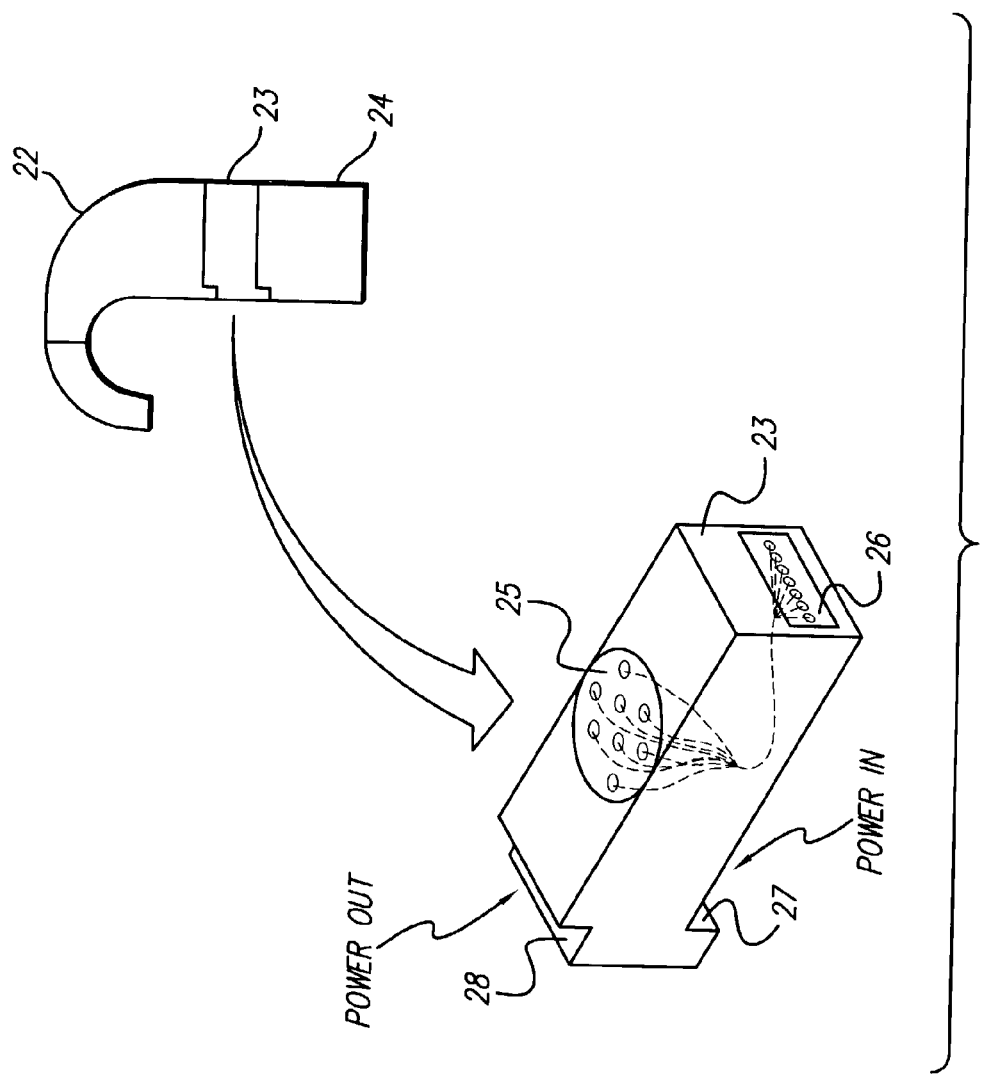
FIG. 1 is shows a simple binaural interposer.

Additional details regarding the CII Bionic Ear™ implant, and the BioNet, or communications network, that may be established between two bionic ears, or other bio-technology-based devices, in accordance with the present invention, including case studies and performance data, may be found in Appendix A of the earlier-referenced provisional patent application Ser. No. 60/313,694; filed Aug. 20, 2001, previously incorporated herein by reference.

Corresponding reference characters indicate corresponding components throughout the several views of the drawings.

DETAILED DESCRIPTION OF THE INVENTION

The following description is of the best mode presently contemplated for carrying out the invention. This description is not to be taken in a limiting sense, but is made merely for the purpose of describing the general principles of the invention.

Turning first to FIG. 1, there is shown a simple binaural interposer 23 that may be used as part of the invention. The BTE speech processor 22 is normally connected to a removable battery 24. To insert the interposer 23, the battery 24 is removed from the BTE processor 22, and the interposer 23 is inserted between the BTE processor 22 and the battery 24. The battery 24 may then be connected to the underneath side of the interposer 23.

The interposer 23 has a BTE interface port 25 on the side thereof that is placed against the BTE processor. Such interface port allows electrical connections to be made with the circuits within the BTE processor. A binaural communications port 26 is on one side of the interposer 23. This port, used for a wired implementation, allows a cable to be attached thereto that connects with another BTE processor, or to a programming device, such as a host fitting station. Power connections or terminals are also provided on the interposer 23 so as to allow the power terminals on the battery 24 to make electrical connection with the power input terminals on the BTE speech processor 22. Thus, Power In terminals are located on a side 27 of the interposer 23 that is placed adjacent the battery terminals, and Power OUT terminals are located on a side 28 of the interposer that is placed adjacent the BTE processor, thereby allowing power to pass through the interposer from the battery to the BTE processor.

Figure 2:
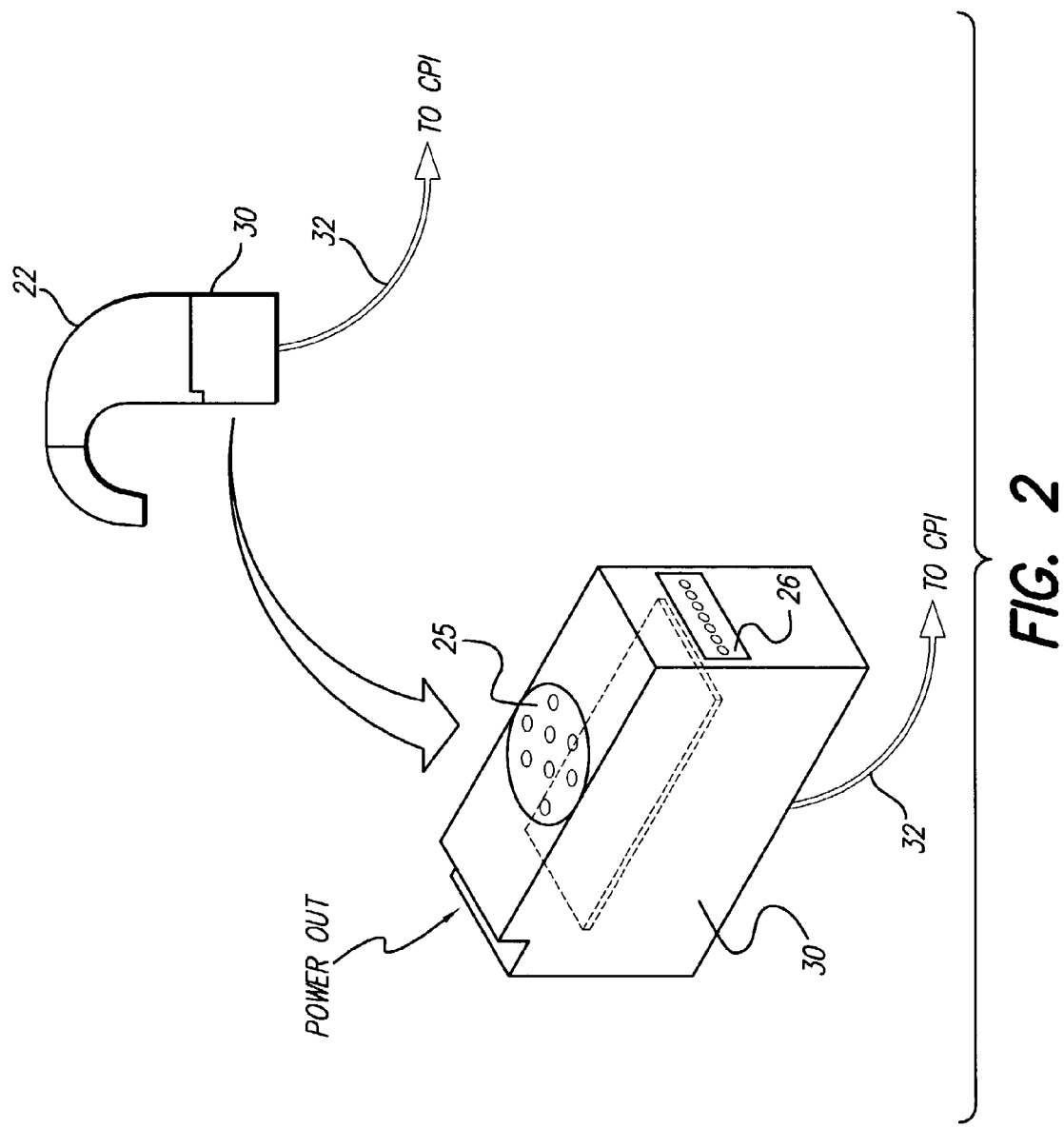
FIG. 2 shows a binaural programming cable suitable for use with a Clinician Programming Interface (CPI) device.

Turning next to FIG. 2, an enhanced binaural interposer 30 is depicted that includes a binaural CPI programming cable 32 exiting from a bottom side thereof. The acronym CPI stands for "clinician programming interface", and refers to a special interface unit that allows the clinician's programmer (usually a laptop computer) to interface with the BTE processor that is being programmed. The CPI programming cable 32 is an extension to an existing BTE/CPI Programming Cable. On one end it is terminated with a standard DB15 connector for connection to a standard CPI-2. On the other end, it is terminated with the enhanced binaural interposer 30. The enhanced interposer 30 performs CPI signal level shifting, power distribution and BSP (body speech processor) interconnection between a Master BTE (to which the interposer is attached), a slave BTE (to which the interposer is tethered) and the CPI (host PC). This is used for wired fitting of the system. Multiple variations of the enhanced interposer 30 are possible, as described, e.g., in FIGS. 5, 6 and 7, below. The fitting system is embodied in a "Wired Binaural Fitting Mode".

Figure 3:
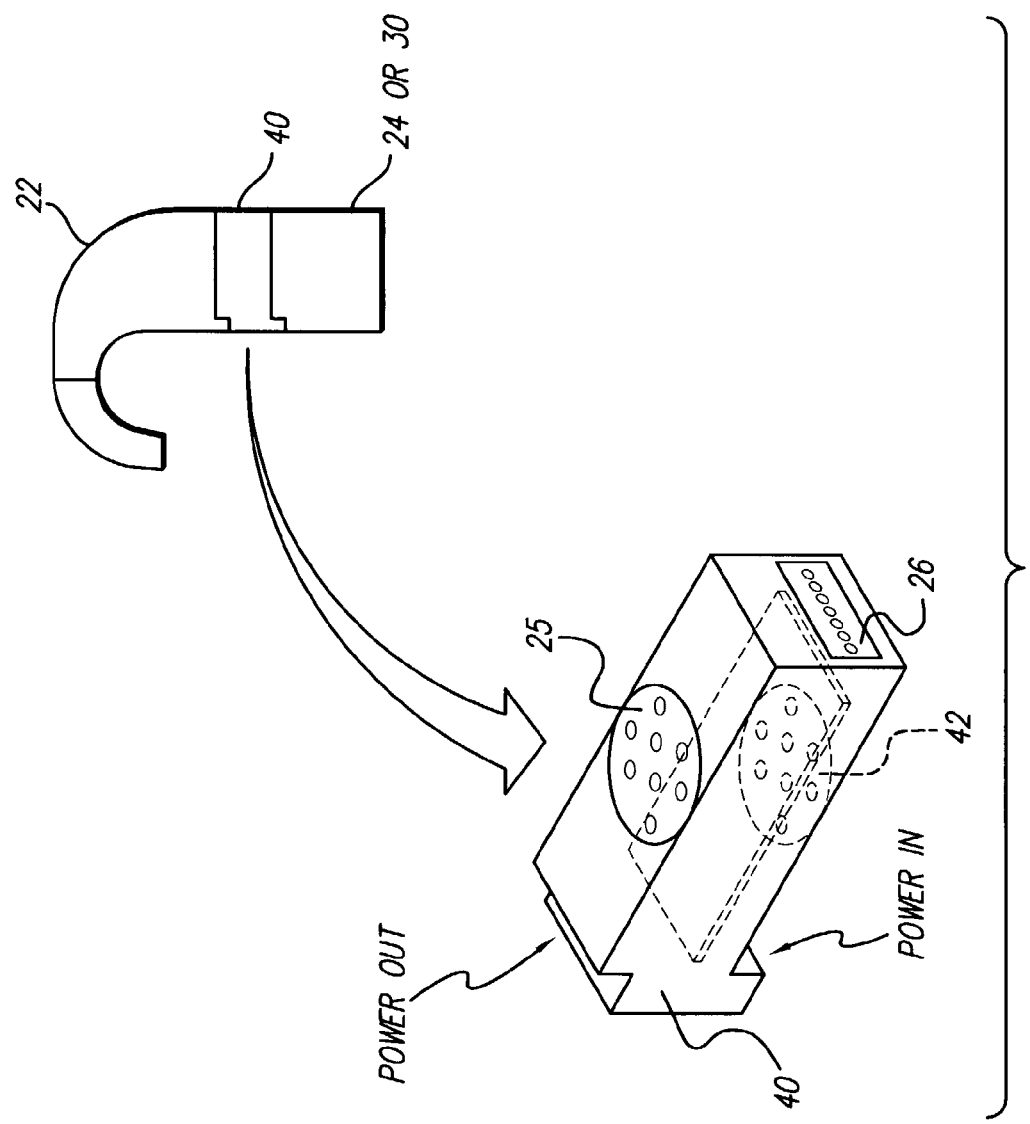
FIG. 3 depicts a BioNet BTE interposer.

Next, with reference to FIG. 3, a BioNet BTE interposer 40 is shown. The interposer 40 houses a wireless transceiver (Bluetooth, ISM, Medical Band, FIS ITEL, etc. . . . ) for wireless communication between binaurally co-joined BTE's and/or a host fitting station. The interposer 40 includes the same or similar connectors, e.g., Power In, Power Out, BTE interface port 25, binaural cable port 26 (optional), and further includes an optional CPI programming cable port 42. In a singular mode, the wireless link provided through the wireless transceiver can be used to fit a remote BTE. A more powerful mode provided by the interposer 40 is simultaneous fitting of synchronized BTE pairs.

Figure 4:
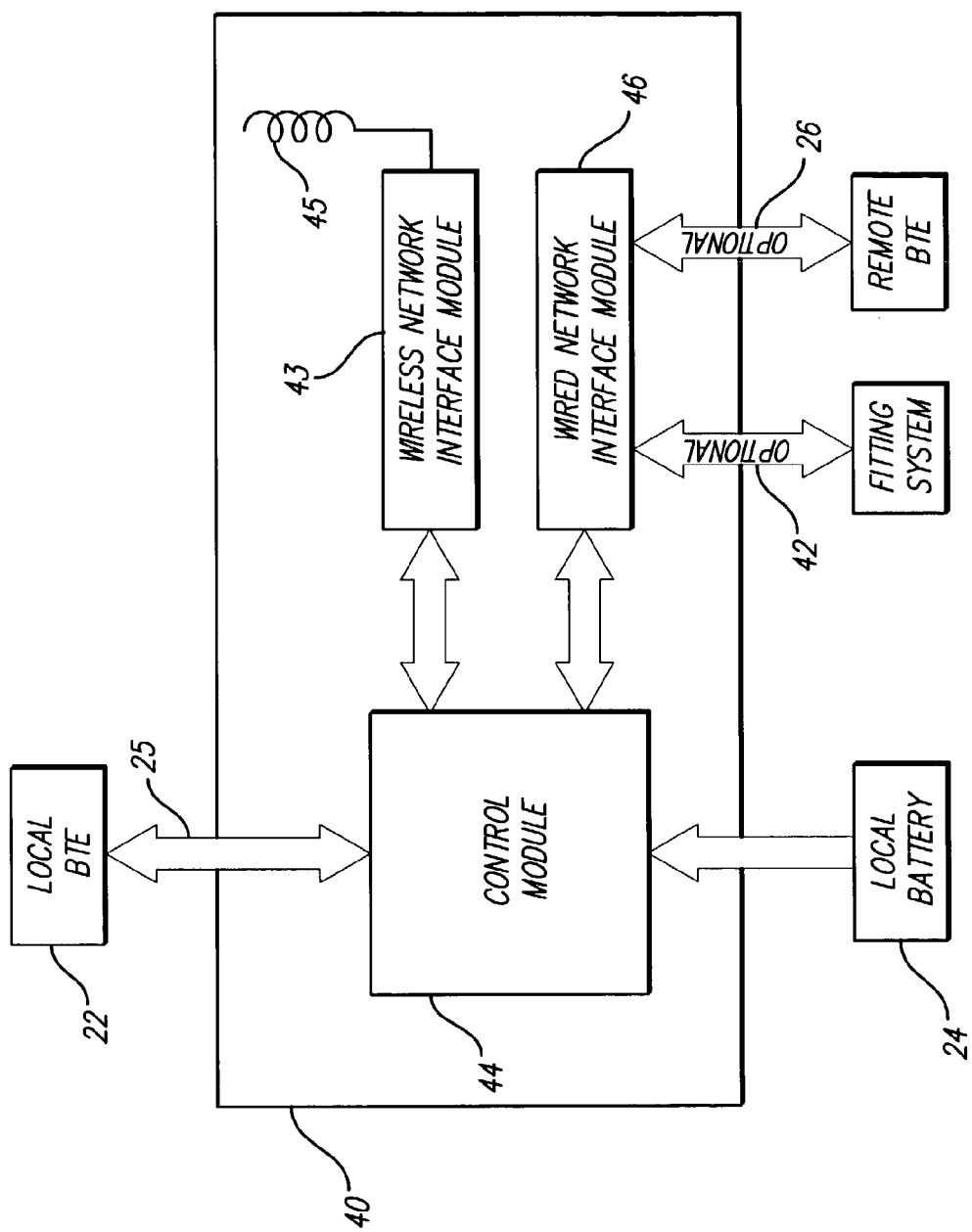
FIG. 4 shows a BioNet Wireless BTE communications controller.

A block diagram of the control subsystem necessary to implement a BioNet is shown in FIG. 4. That which is shown in FIG. 4 functionally represents the circuitry contained within the interposer 40. As seen in FIG. 4, a control module 44 interfaces with the local BTE 22 and local battery 24 through the BTE interface port 25 and power connections. Internal to the interposer 40, the control module 44—typically realized from microprocessor circuitry—interfaces with both a wireless network interface module 43 and a wired network interface module 46. The wireless network interface module 43 has an antenna coil 45 connected thereto. Such antenna coil 45 is advantageously embedded within the housing of the interposer 40 so that it is not obtrusively visible to a user of the BioNet, which BioNet is made possible by the interposer 40. The wireless network interface module 43 may connect to one or more remote BTE's. The wired network interface module 46 may connect to a remote BTE through the binaural cable port 26, or to a host fitting system through the CPI programming cable port 42.

Figure 5:
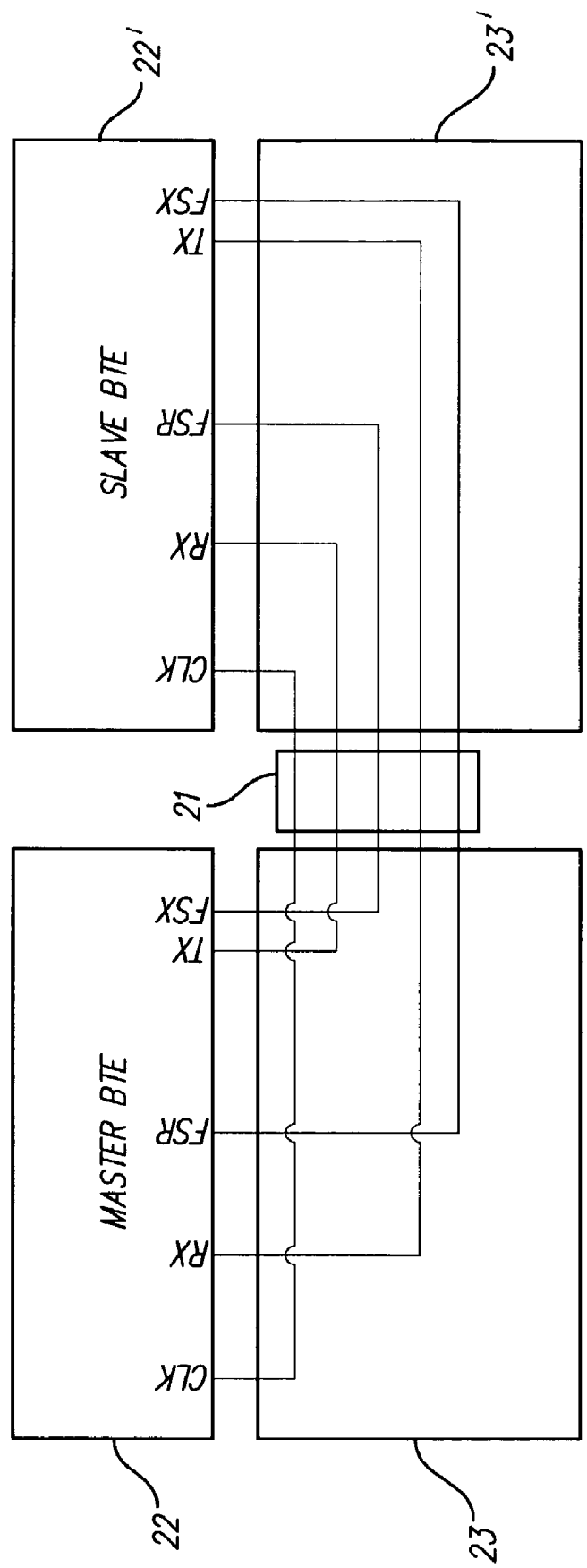
FIG. 5 depicts a first configuration for a binaural fitting cable.
Figure 9:
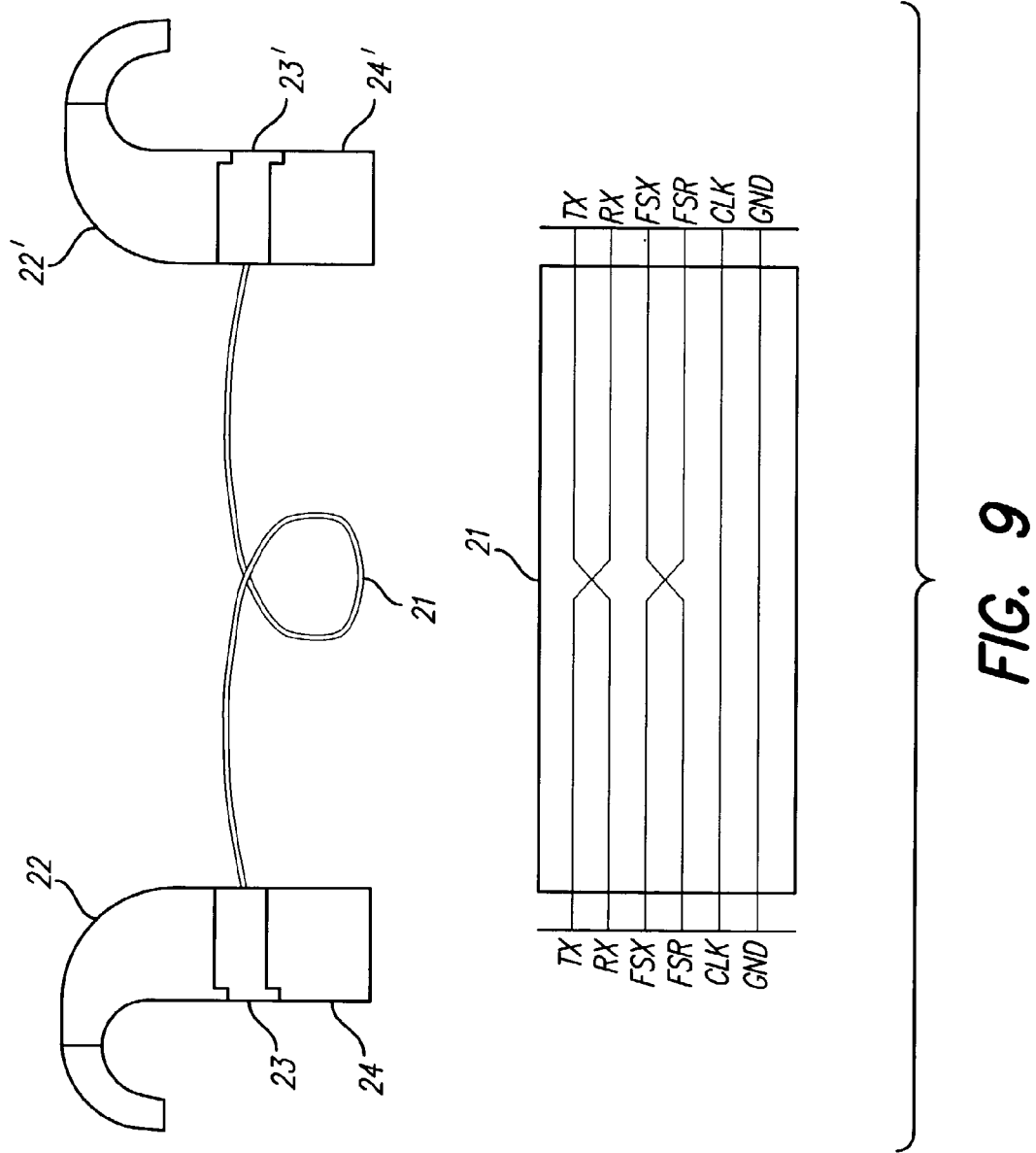
FIG. 9 shows a binaural standalone approach.

FIG. 5 illustrates a standalone wired interconnection of two BTE's, a master BTE 22, and a slave BTE 22', via simple binaural interposers 23 and 23', and a binaural interface cable 21. The wiring of the binaural interface cable 21 is illustrated in FIG. 9.

Figure 6:
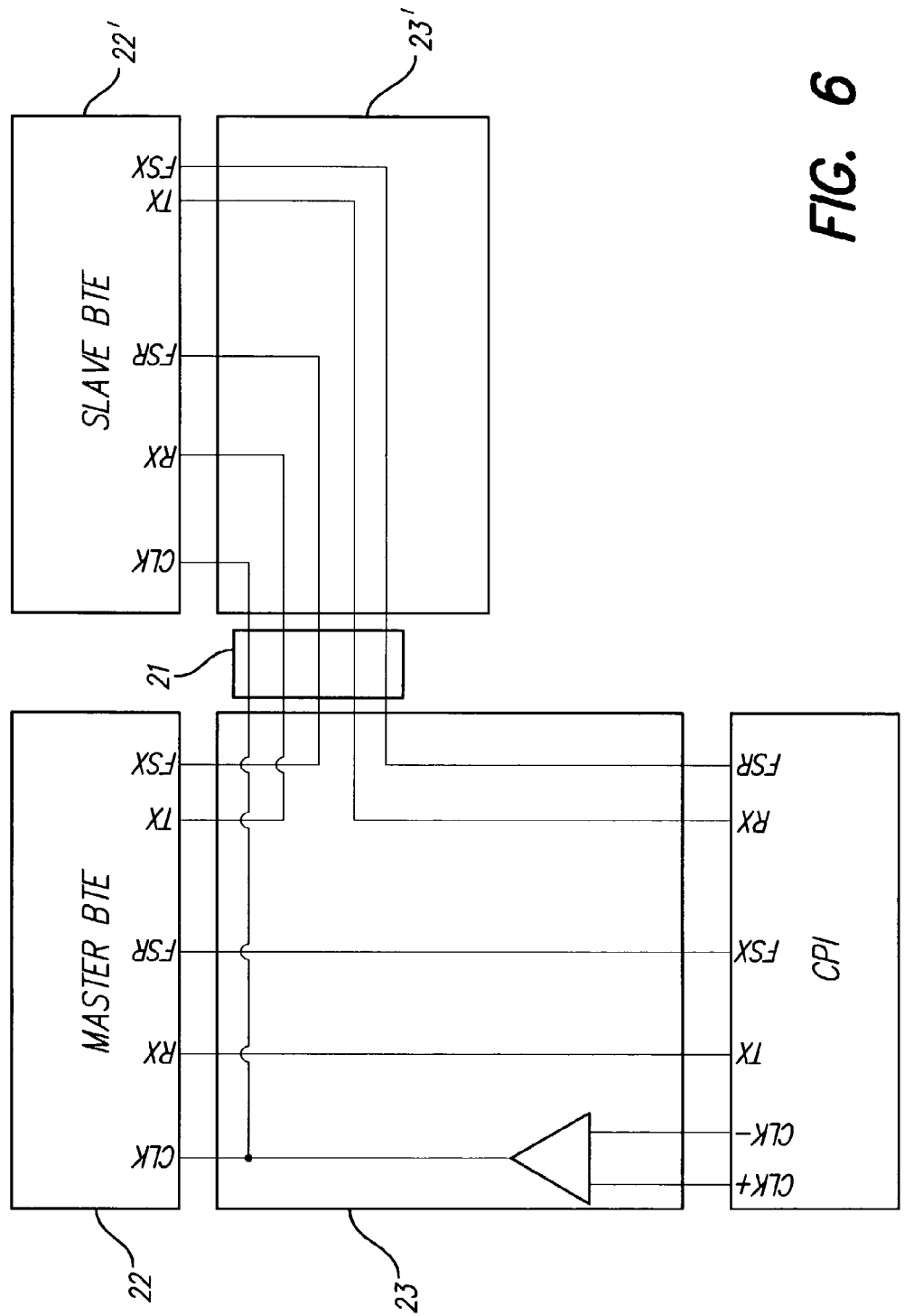
FIG. 6 illustrates a second configuration for a binaural fitting cable.
Figure 7:
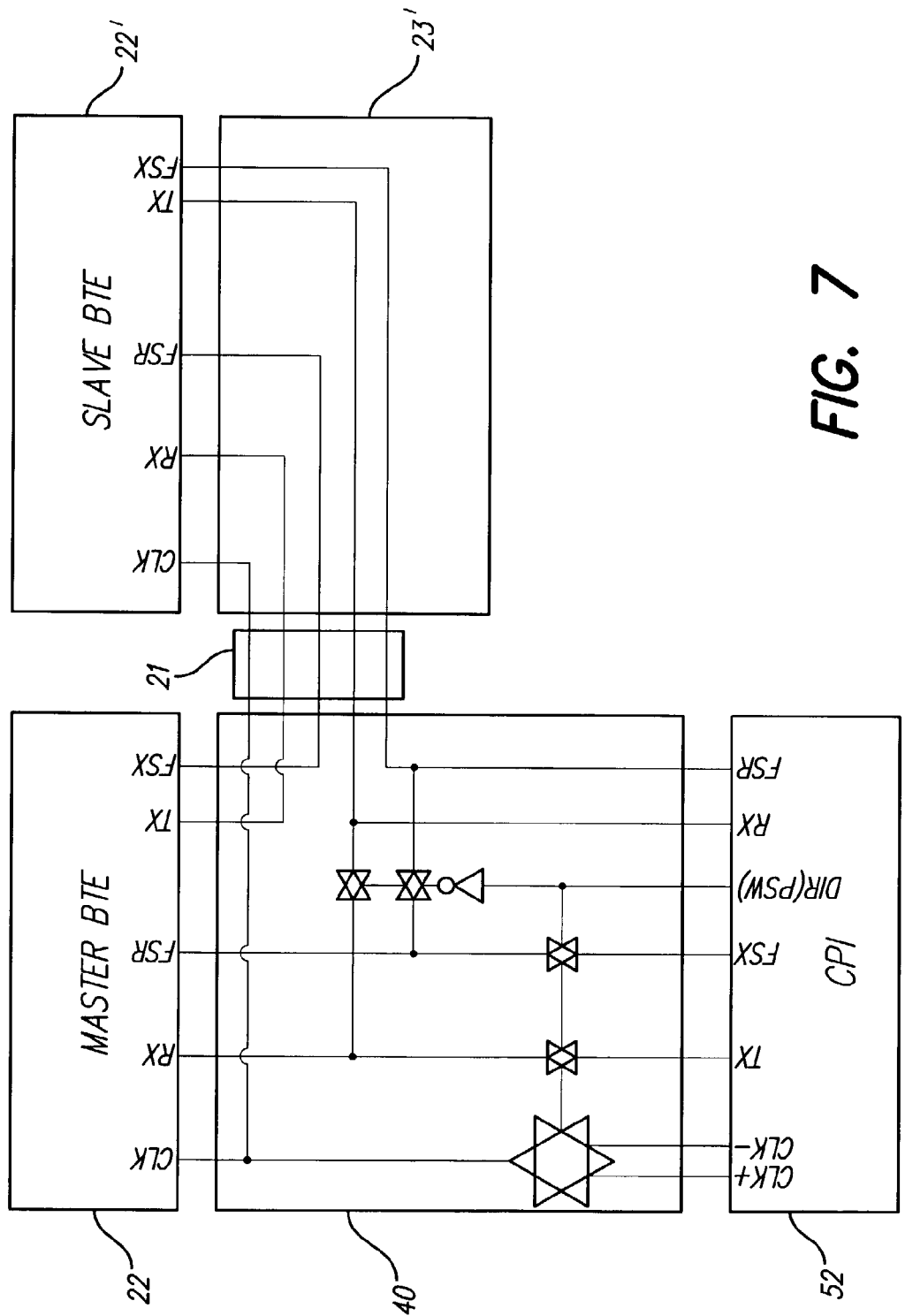
FIG. 7 illustrates a third configuration for a binaural fitting cable.
Figure 8:
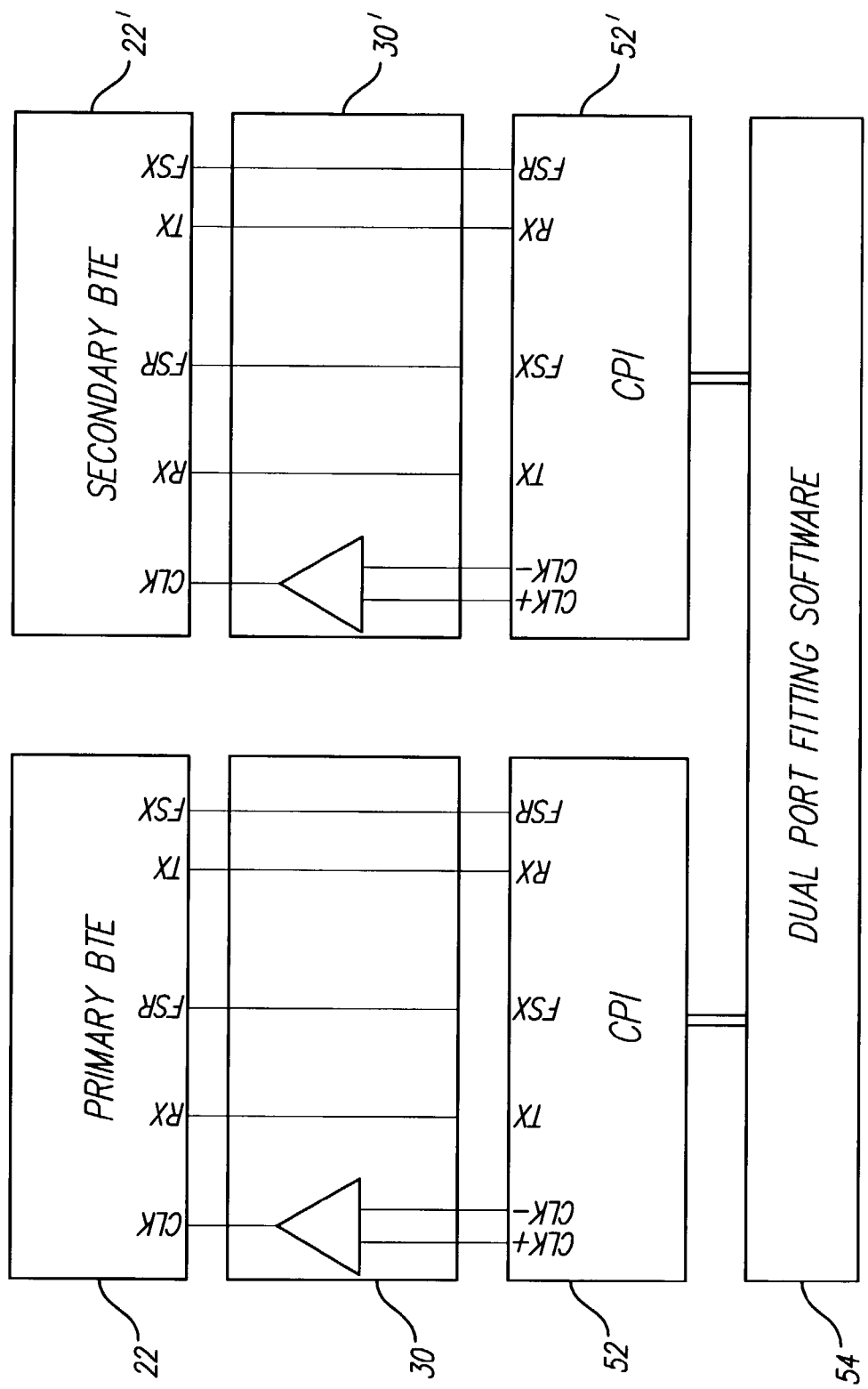
FIG. 8 shows a fourth configuration of a fitting cable.

FIGS. 6, 7 and 8 respectively show variations of a master BTE 22 connected to a slave BTE 22'. In FIG. 6, an enhanced interposer 30 connects the master BTE 22 to a CPI device 52, while a binaural interface cable 21 connects the slave BTE 22' to both the CPI 52 and the master BTE 22 through a simple interposer 23'. In FIG. 7, a BioNet BTE interposer 40 connects the master BTE 22 to a CPI device 52, while a binaural interface cable 21 connects the slave BTE 22' to both the CPI 52 and the master BTE 22 through a simple interposer 23'. In FIG. 8, two enhanced interposers 30 and 30' are used to respectively connect a primary BTE 22 and a secondary BTE 22' to respective CPI's 52 and 52'. Dual Port Fitting Software 54 interfaces with each of the respective CPI's 52 and 52'.

Figure 10:
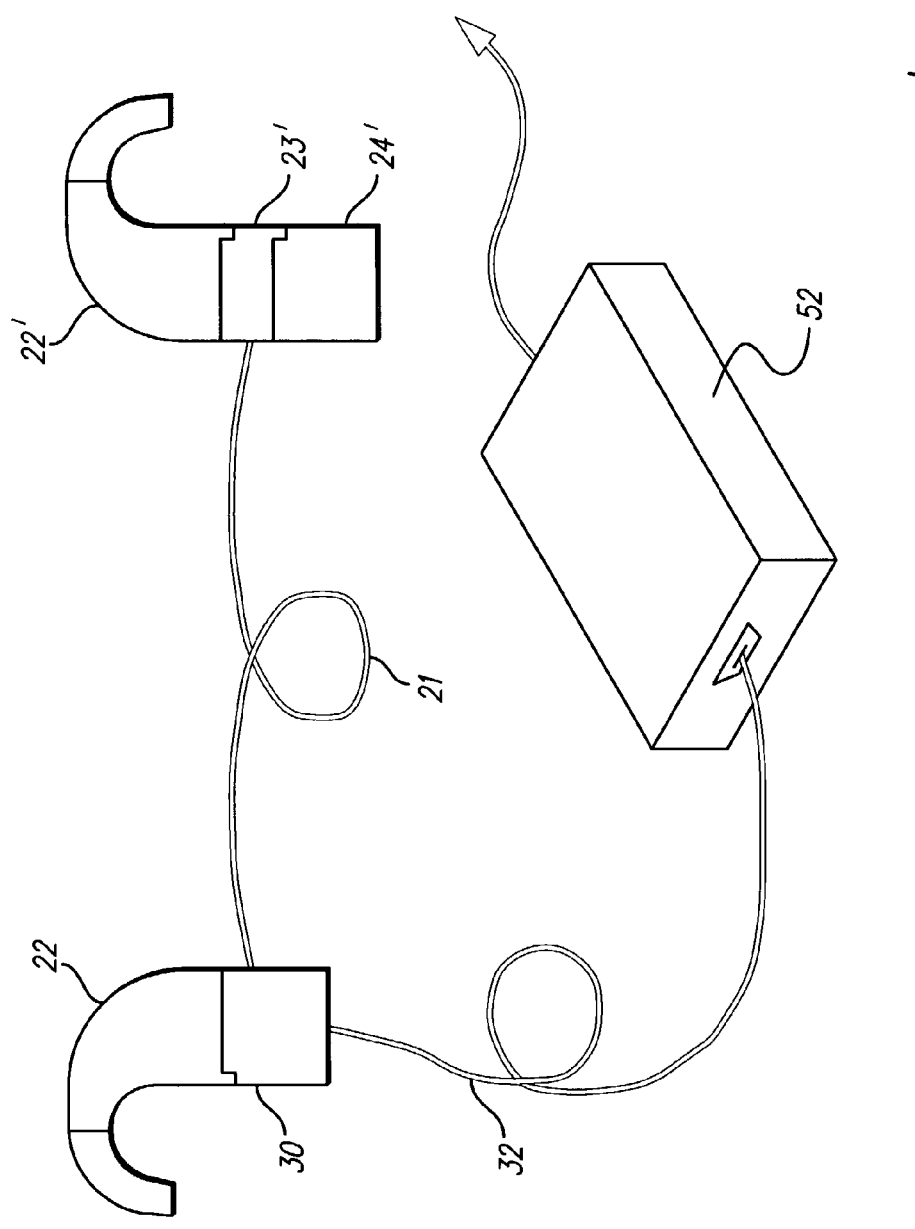
FIG. 10 depicts a wired binaural fitting mode.

Turning next to FIG. 10, a wired binaural fitting mode is illustrated. A slave BTE 22' is connected through, e.g., a simple interposer 23' and a synchronous binaural interface cable 21 to an enhanced interposer 30. The enhanced interposer 30 is connected to a master BTE 22. The binaural fitting cable 32 that exits from the enhanced interposer 30 (see FIG. 2) is connected to a CPI device 52. The CPI device 52, in turn, is connected to a host programming system, e.g., a laptop computer (not shown) loaded with the appropriate fitting software.

Figure 11:
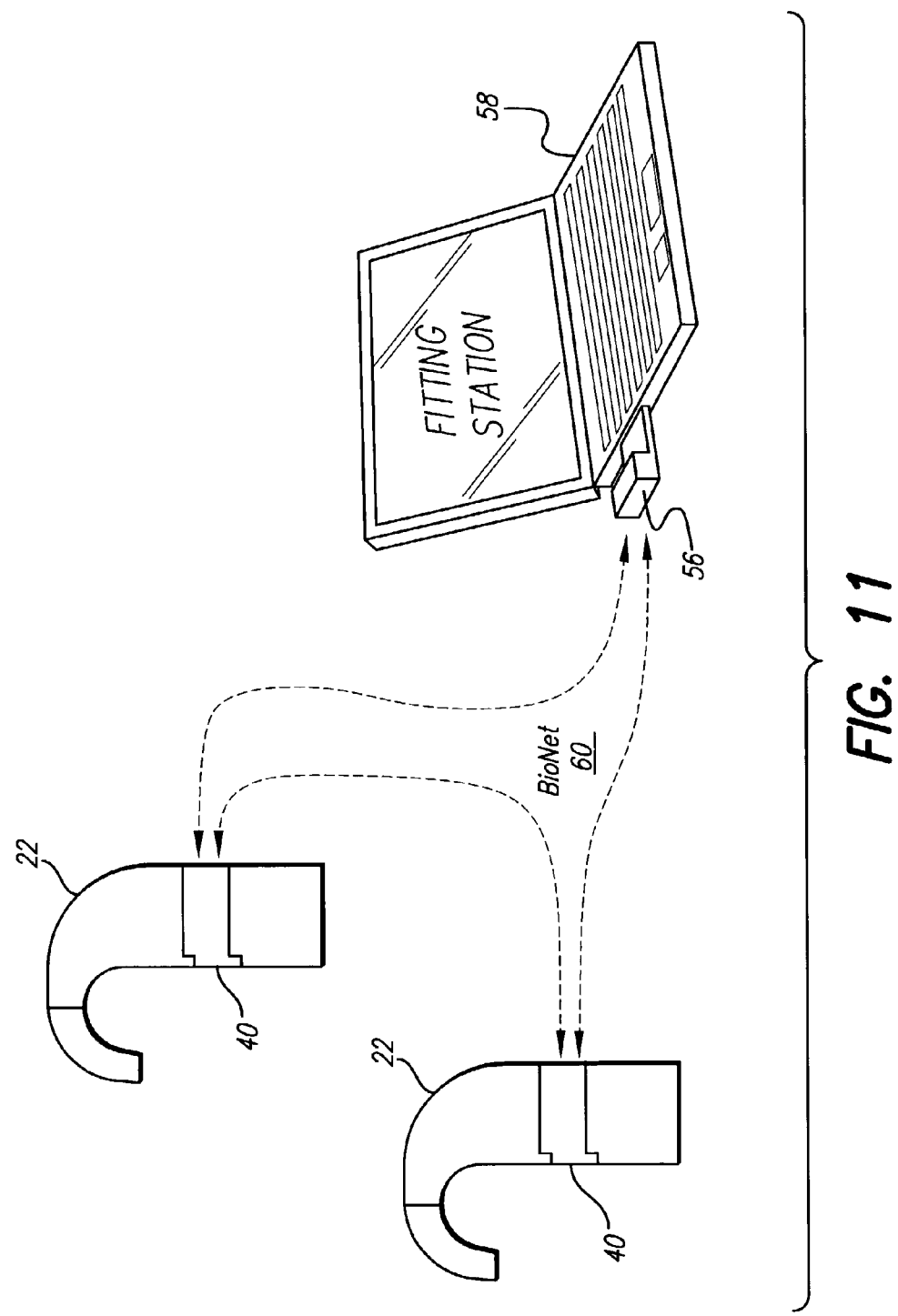
FIG. 11 shows a BioNet Wireless fitting system.

Next, with reference to FIG. 11, a BioNet Wireless Fitting System is illustrated. FIG. 11 embodies the operational modes for fitting and operating a wireless BTE fitting system. As seen in FIG. 11, the system consists of two BioNet BTE Interposers 40, each connected to a respective BTE 22, and a BioNet PC Card 56 plugged into the host fitting station 58. As thus configured, a BioNet 60 is created that allows either BTE to be coupled to the host fitting station 58, and that further allows either BTE to be coupled to the other BTE.

Figure 12:
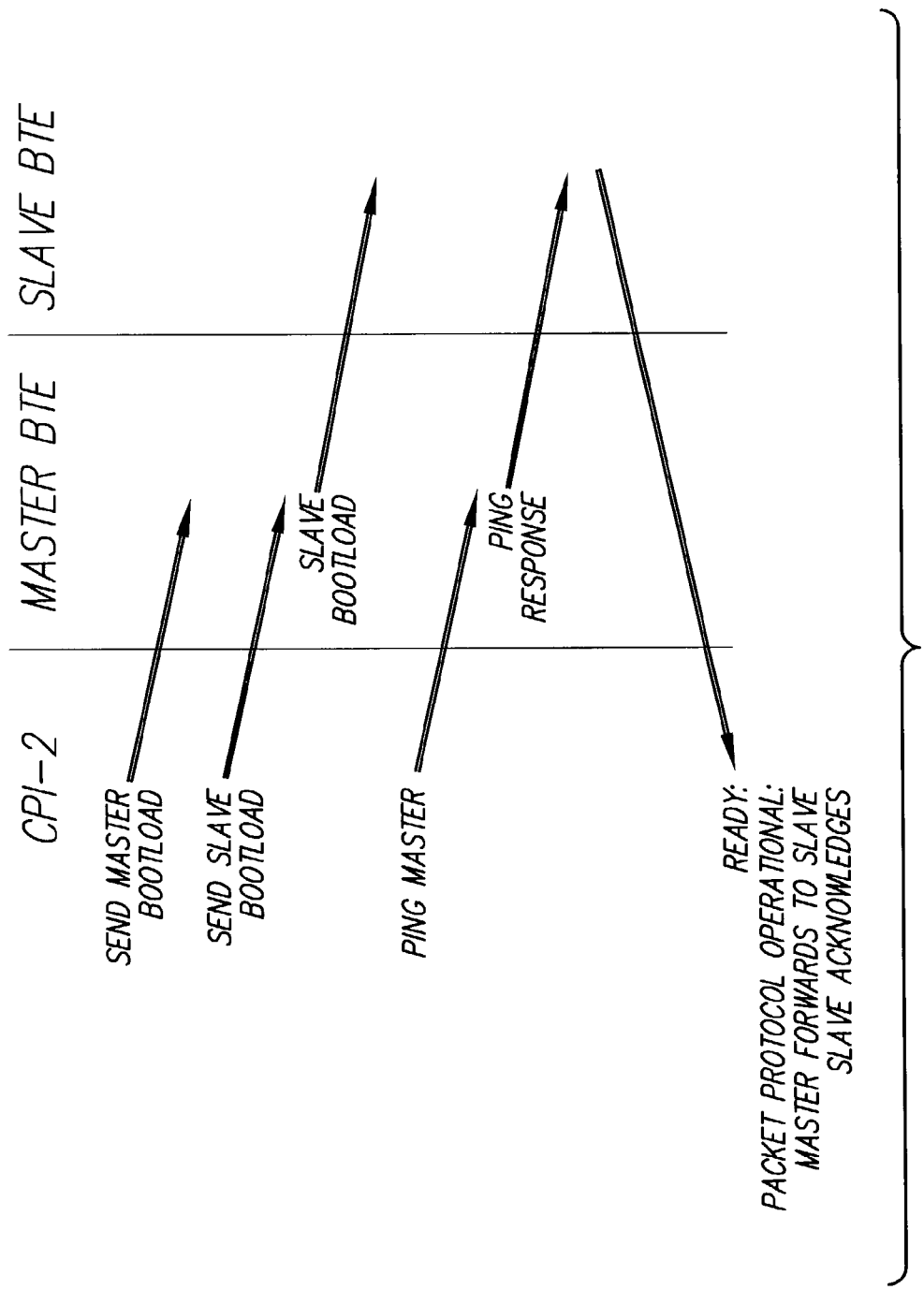
FIG. 12 illustrates a cascaded master/slave bootload operation.

FIG. 12 illustrates the preferred cascaded Master/Slave bootload operation relative to a CPI device, a Master BTE and a Slave BTE. As seen from FIG. 12, in keeping with the architecture of present day speech processors, a cascaded bootload scenario is presented whereby cable interconnection as per "Fitting Cable Configuration #2", FIG. 6, is employed. The "Command/Response" handshaking is defined in the serial link protocol and is presently controlled from the PC side by PPMIF.DLL (or equivalent). First, the need to utilize multiple target addresses (destination field in the packet protocol) is required. Secondly, monitor functions running on the DSP require master & slave awareness with all incoming commands (from the host) delivered to the master for processing or forwarding (based on destination address) and all acknowledges to the PC delivered from the slave (directly or by way of forwarding from the master).

The key to the startup is a double blind bootload. That is, bootloading is a blind process, the success of which cannot be determined until the operation is complete and a PING is received from the remote kernel. In one binaural configuration, this blind operation is cascaded. For the BTE processor to become operational, a bootload to the master is performed (identical to the present day single speech processor environment). Upon completing the master bootload sequence, the slave bootload sequence is forwarded by the now operational master BTE to the slave BTE. Once both BTE's have been bootloaded, success can be determined by issuing a PING to the master BTE. The ping response is routed through the slave BTE and returned to the host PC through the CPI. Receipt of this acknowledgment indicates success.

Once a bootload has been successfully made, application programs can be loaded as per an existing packet protocol with the caveat that destination addresses will determine which BTE processor processes each command.

Figure 13:
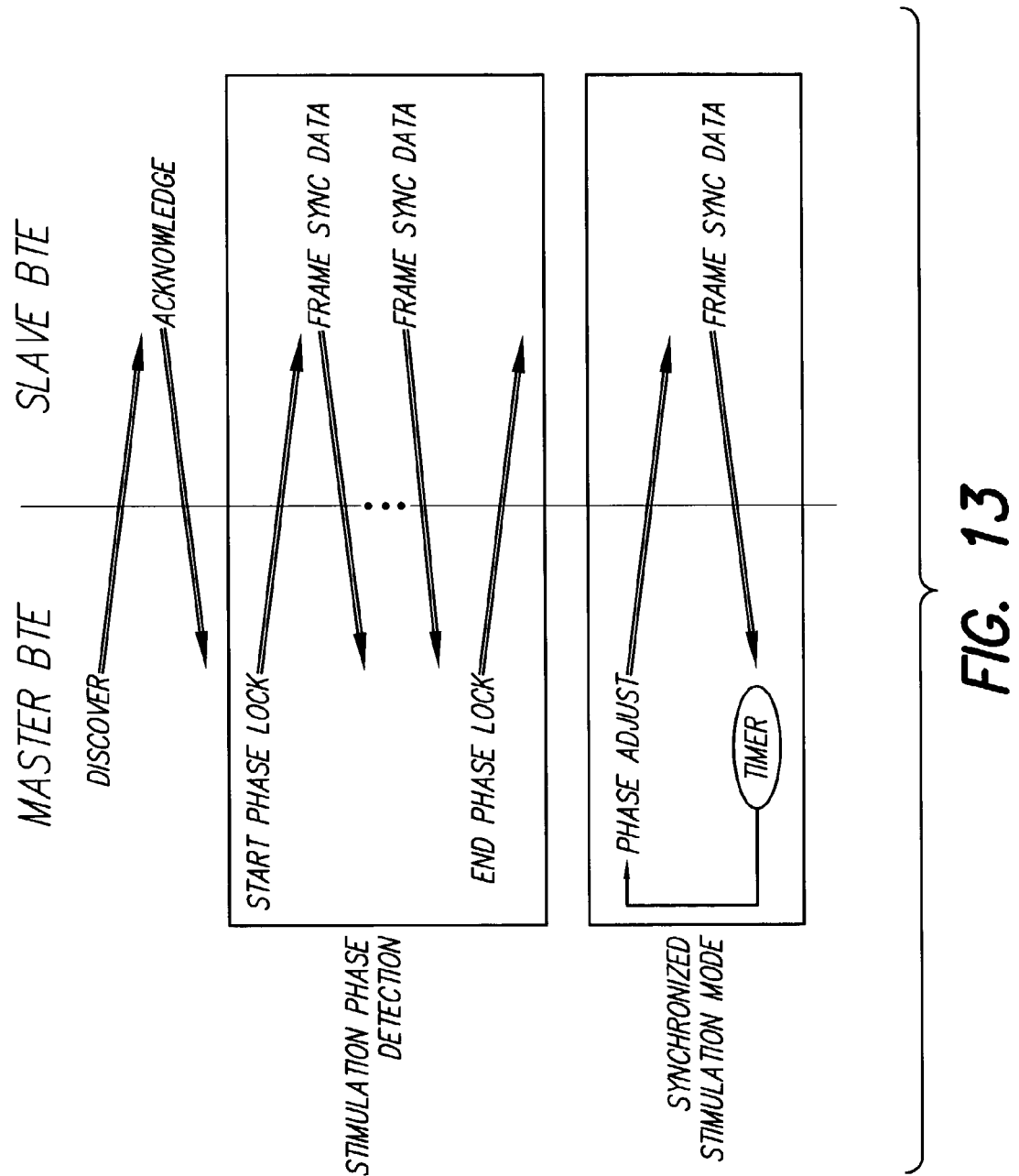
FIG. 13 shows stimulation synchronization.

FIG. 13 illustrates how stimulation synchronization is obtained between the Master BTE and the Slave BTE.

Figure 14:
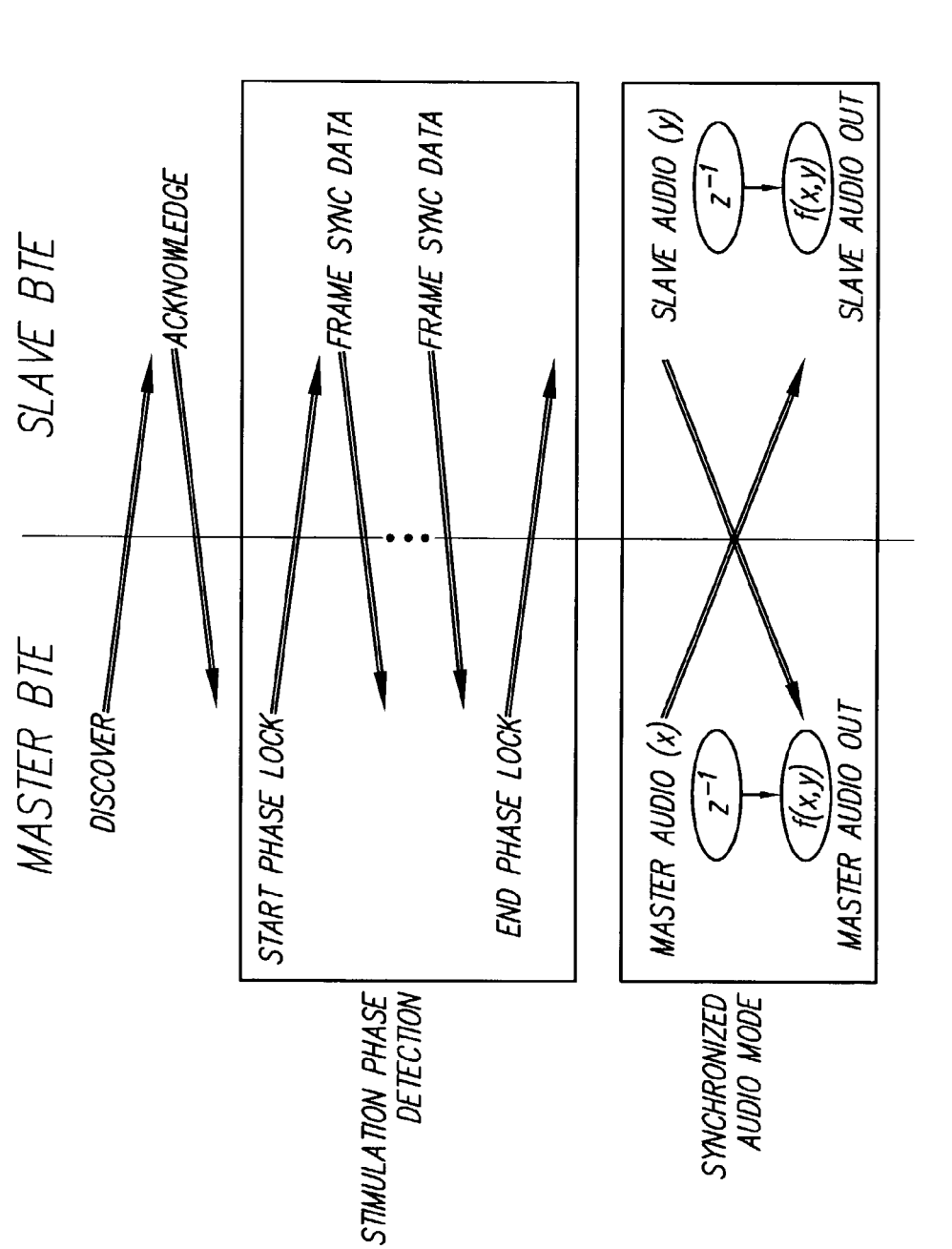
FIG. 14 depicts audio synchronization.

FIG. 14 shows the manner in which audio synchronization is obtained between the Master BTE and the Slave BTE.

Figure 15:
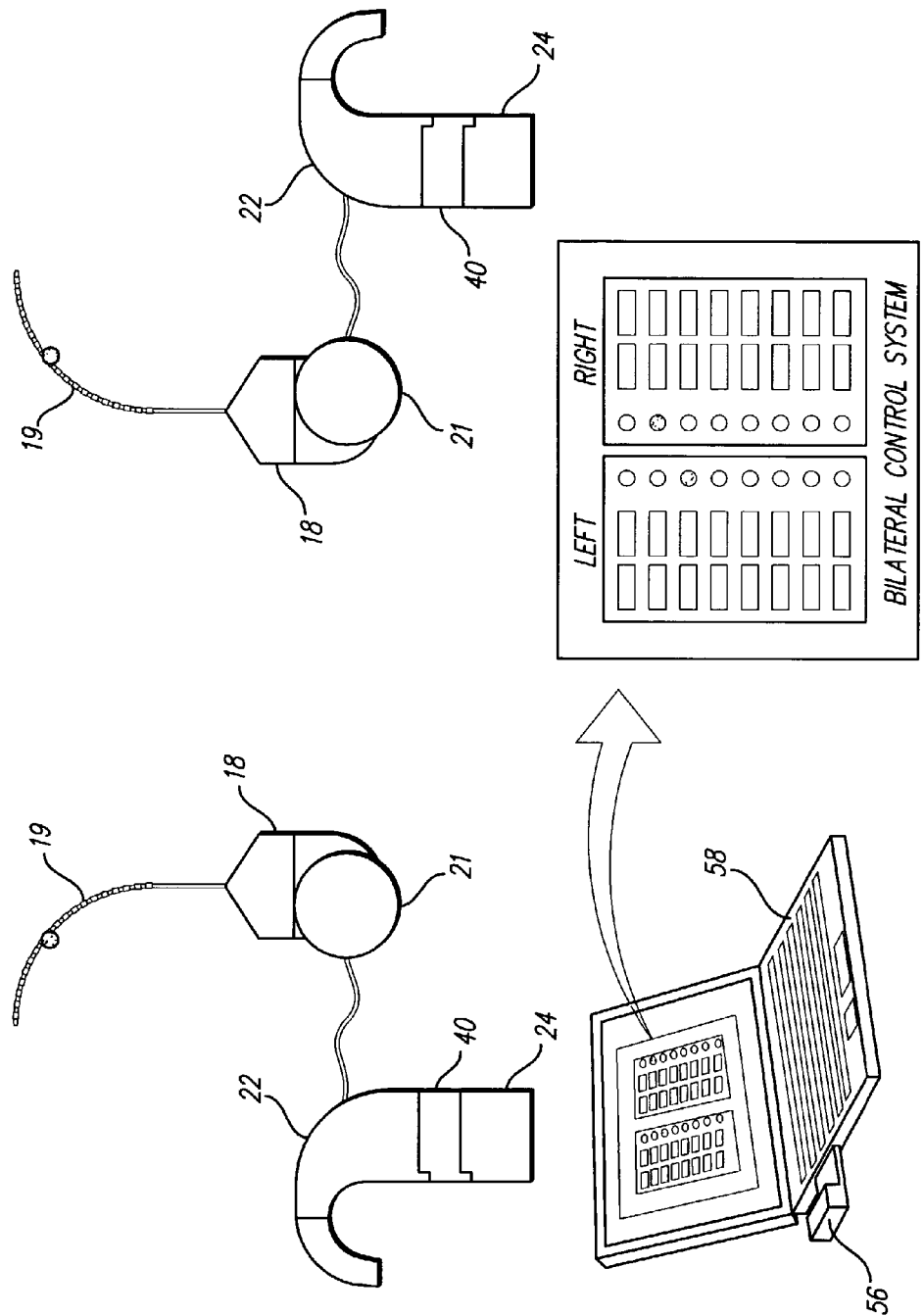
FIG. 15 illustrates a fitting system framework.

FIG. 15 depicts a fitting system platform. Such platform allows operation with the various binaural speech processor configurations described above. The platform includes a host fitting station 58, typically comprising a laptop computer loaded with the appropriate fitting software. Also included in the platform is a BioNet PC card 56, or equivalent, that is plugged into the fitting station 58, thereby allowing communications with two BTE's 22, one BTE being for the left ear and the other BTE being for the right ear. Each BTE is coupled to a headpiece 21. The headpiece 21, in turn, is coupled to the bionic ear implant 18, which implant includes an electrode array 19. A multiplicity of electrode contacts, e.g., 16 electrode contacts, are spaced apart along the length of the array 19, thereby allowing stimulation of cochlea tissue to occur at various locations along the length of the array.

Figure 16:
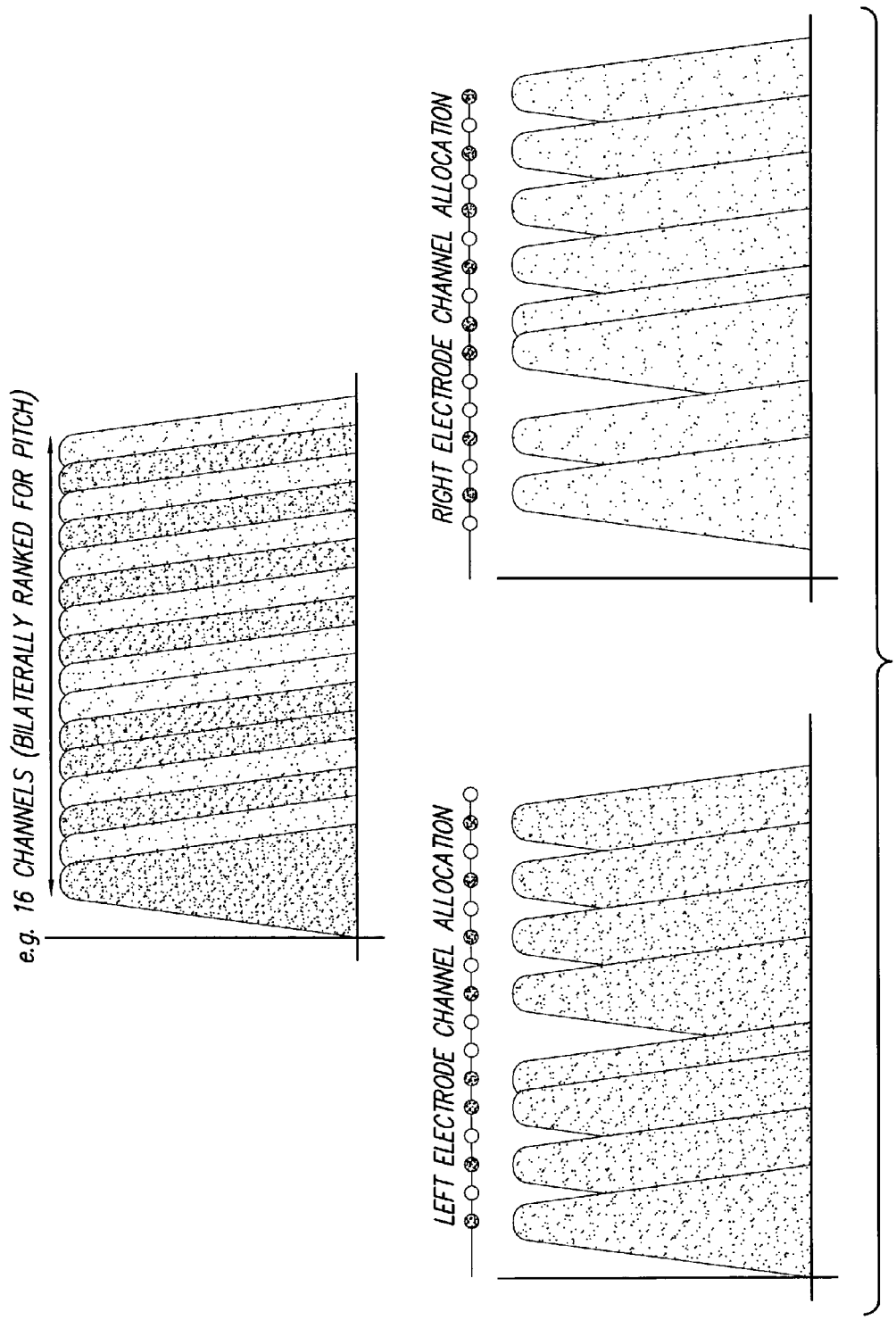
FIG. 16 conceptually illustrates a bilateral fitting paradigm.

Fundamental to the platform shown in FIG. 15 are means to perform bilateral pitch ranking and channel allocation. This process of pitch ranking is illustrated in FIG. 16, and is further explained in Appendix A of the above-referenced provisional patent application Ser. No. 60/313,694, filed Aug. 20, 2001, previously incorporated herein by reference.

While the invention herein disclosed has been described by means of specific embodiments and applications thereof, numerous modifications and variations could be made thereto by those skilled in the art without departing from the scope of the invention set forth in the claims.

What is claimed is:

1. A bilateral cochlear implant system comprising:
   a local bionic ear system having a local BTE unit associated therewith, and a remote bionic ear system having a remote BTE unit associated therewith, each BTE unit comprising a processor, a battery module and a cochlear array;
   two interposer modules, one adapted to be inserted between the processor and battery module of the local BTE unit, and the other adapted to be inserted between the processor and battery module of the remote BTE unit;
   communication channel means for allowing signal communications to take place between the local BTE unit and the remote BTE unit;
   synchronization means for synchronizing the signal communications that occur over the communication channel means; and
   a bilateral fitting paradigm for cooperatively programming the local BTE unit and the remote BTE unit, wherein the bilateral fitting paradigm uses trans-cochlear pitch discrimination, wherein pitch discrimination reduces channel interaction and optimally interleaves channel information across available electrode contacts.

2. The bilateral cochlear implant system of claim 1 wherein each of the interposer modules comprises a binaural interposer module (23) having a binaural communications port (26) into which an interface cable (21) is adapted to be detachably connected for coupling to another interposer module, thereby providing a direct wired network connection between the two BTE units.

3. The bilateral cochlear implant system of claim 1 wherein at least one of the interposer modules comprises an interposer module (30), the interposer module having:
   a binaural communications port (26) into which an interface cable (21) is adapted to be detachably connected for coupling to another interposer module, thereby providing a direct wired network connection between the two BTE units, and
   a binaural fitting cable (32) adapted for connection to a host clinician programming interface (CPI) unit.

4. The bilateral cochlea implant system of claim 1 wherein at least one of the interposer modules comprises a network BTE interposer module having built-in wireless communication transceiver for allowing signal communications with another network BTE interposer module.

5. The bilateral cochlear implant system of claim 4 wherein the wireless communication transceiver further allows signal communications with a host clinician programming interface (CPI) unit.

6. The bilateral cochlear implant system of claim 1 wherein at least one of the interposer units comprises first connection means for making electrical and mechanical connection with the respective BTE unit;

second connection means for making electrical and mechanical connection with the battery module adapted for use with the respective BTE unit;

a control unit (44) operatively coupled to the first and second connection means;

a wireless network interface module (43) coupled to the control unit, wherein the wireless network interface module has an antenna (45) through which wireless communications may take place; and a wired network interface module (46) coupled to the control unit, wherein the wired network interface module has a remote BTE connection port (26) and a fitting system port (42) through which wired communications with the remote BTE or a clinician programming interface (CPI) unit may optionally take place.

7. The bilateral cochlear implant system of claim 1 wherein the channel communication means includes means for performing a cascaded master/slave bootload operation.

* * * * *